United States Patent
Bair et al.

(10) Patent No.: US 7,780,916 B2
(45) Date of Patent: Aug. 24, 2010

(54) FLOW CYTOMETER SYSTEM WITH UNCLOGGING FEATURE

(75) Inventors: Nathaniel C. Bair, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 3 days.

(21) Appl. No.: 11/735,456

(22) Filed: Apr. 14, 2007

(65) Prior Publication Data

US 2008/0092961 A1    Apr. 24, 2008

Related U.S. Application Data

(63) Continuation-in-part of application No. 11/370,714, filed on Mar. 8, 2006.

(60) Provisional application No. 60/792,536, filed on Apr. 17, 2006.

(51) Int. Cl.
*G01N 21/00* (2006.01)
*E03B 1/00* (2006.01)
*B01L 3/02* (2006.01)
*G01N 15/06* (2006.01)
*G01N 35/02* (2006.01)

(52) U.S. Cl. ............... 422/81; 422/62; 422/67; 422/68.1; 422/100; 422/101; 436/50; 436/52; 137/7; 137/12

(58) Field of Classification Search .................. None
See application file for complete search history.

(56) References Cited

U.S. PATENT DOCUMENTS

| | | | |
|---|---|---|---|
| 3,672,402 A | 6/1972 | Bloemer |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,790,653 A | 12/1988 | North, Jr. |
| 4,818,103 A | 4/1989 | Thomas et al. |
| 4,844,610 A | 7/1989 | North, Jr. |
| 5,040,890 A | 8/1991 | North, Jr. |
| 5,043,706 A | 8/1991 | Oliver |
| 5,083,862 A | 1/1992 | Rusnak |

(Continued)

FOREIGN PATENT DOCUMENTS

EP    1521076    9/2004

(Continued)

*Primary Examiner*—Jill Warden
*Assistant Examiner*—Neil Turk
(74) *Attorney, Agent, or Firm*—Jeffrey Schox

(57) ABSTRACT

The fluidic system with an unclogging feature of the preferred embodiment includes a flow channel, a sheath pump to pump sheath fluid from a sheath container into an interrogation zone, and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The pump and controller cooperate to propagate a pulsation through the flow channel from the pump if the flow channel is clogged. The fluidic system is preferably incorporated into a flow cytometer with a flow cell that includes the interrogation zone.

19 Claims, 1 Drawing Sheet

U.S. PATENT DOCUMENTS

| | | |
|---|---|---|
| 5,155,543 A | 10/1992 | Hirako |
| 5,395,588 A | 3/1995 | North, Jr. |
| 5,403,552 A | 4/1995 | Pardikes |
| 5,539,386 A | 7/1996 | Elliot |
| 5,552,885 A | 9/1996 | Steen |
| 6,039,078 A | 3/2000 | Tamari |
| 6,110,427 A | 8/2000 | Uffenheimer |
| 6,156,208 A | 12/2000 | Desjardins et al. |
| 6,183,697 B1 | 2/2001 | Tanaka |
| 6,288,783 B1 | 9/2001 | Auad |
| 6,382,228 B1 | 5/2002 | Cabuz |
| 6,427,521 B2 | 8/2002 | Jakkula et al. |
| 6,568,271 B2 | 5/2003 | Shah et al. |
| 6,602,469 B1 | 8/2003 | Maus et al. |
| 6,694,799 B2 | 2/2004 | Small |
| 6,825,926 B2 | 11/2004 | Turner et al. |
| 6,852,284 B1 | 2/2005 | Holl et al. |
| 6,872,180 B2 | 3/2005 | Reinhardt et al. |
| 6,908,226 B2 | 6/2005 | Siddiqui et al. |
| 6,912,904 B2 | 7/2005 | Storm, Jr. et al. |
| 6,941,005 B2 | 9/2005 | Lary et al. |
| 7,019,834 B2 | 3/2006 | Sebok et al. |
| 7,061,595 B2 | 6/2006 | Cabuz |
| 2002/0028434 A1 | 3/2002 | Goix |
| 2002/0059959 A1 | 5/2002 | Qatu et al. |
| 2002/0123154 A1 | 9/2002 | Burshteyn et al. |
| 2003/0054558 A1 | 3/2003 | Kurabayashi |
| 2003/0062314 A1 | 4/2003 | Davidson et al. |
| 2003/0072549 A1 | 4/2003 | Facer et al. |
| 2003/0129090 A1 * | 7/2003 | Farrell ................... 422/68.1 |
| 2003/0202175 A1 | 10/2003 | Van den Engh et al. |
| 2003/0211009 A1 | 11/2003 | Buchanan |
| 2003/0223061 A1 | 12/2003 | Sebok et al. |
| 2004/0031521 A1 | 2/2004 | Vrane et al. |
| 2004/0112808 A1 | 6/2004 | Takagi et al. |
| 2004/0123645 A1 | 7/2004 | Storm, Jr. et al. |
| 2005/0069454 A1 | 3/2005 | Bell |
| 2005/0195684 A1 | 9/2005 | Mayer |
| 2005/0252574 A1 | 11/2005 | Khan et al. |
| 2006/0286549 A1 | 12/2006 | Sohn |
| 2007/0003434 A1 | 1/2007 | Padmanabhan et al. |

FOREIGN PATENT DOCUMENTS

| | | |
|---|---|---|
| EP | 1521076 | 4/2005 |
| WO | 2005017499 | 8/2004 |
| WO | WO/2005/017499 | 2/2005 |

* cited by examiner

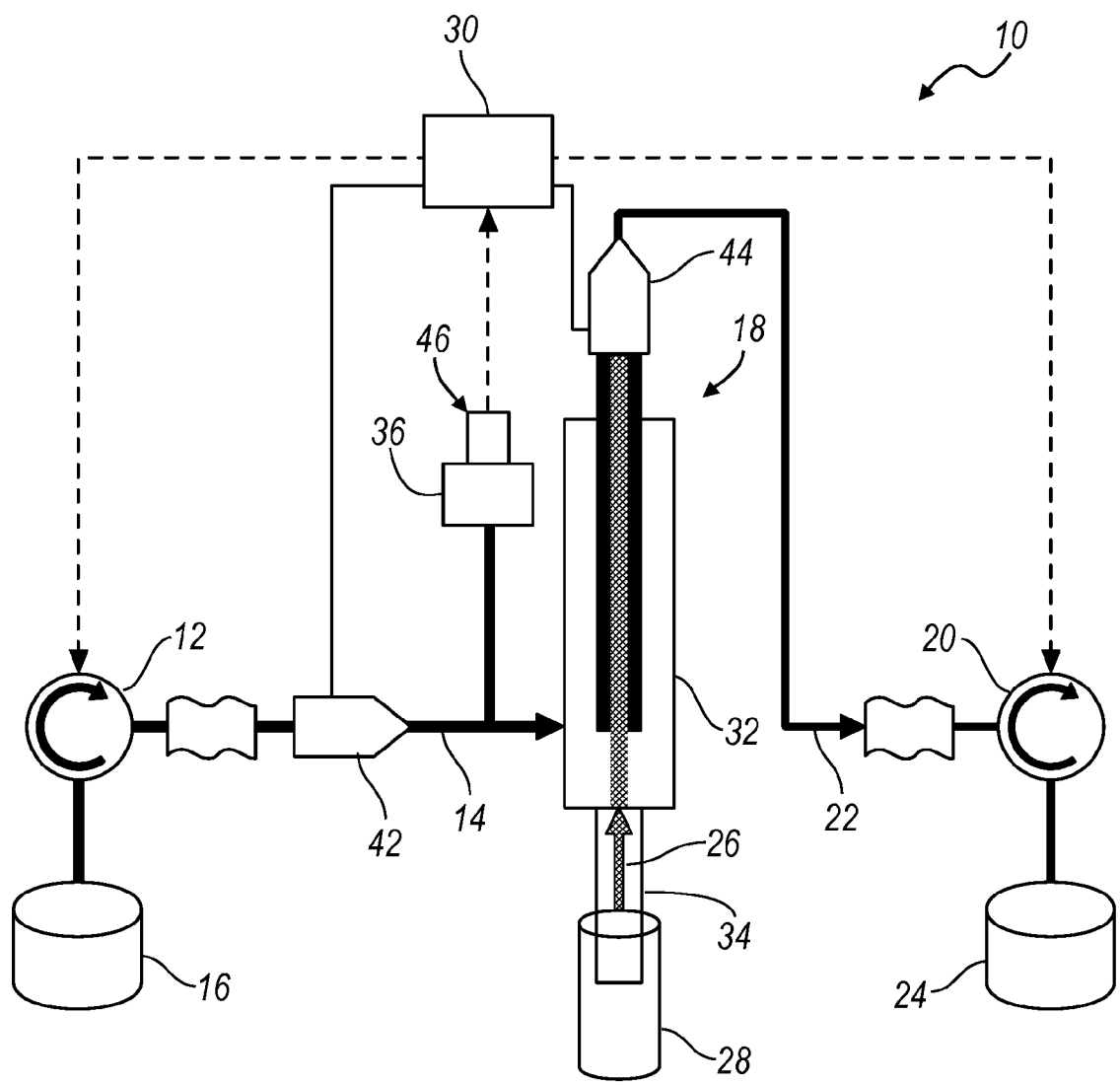
FIGURE is a Continuation-in-Part of U.S. application Ser. No. 11/370,714, filed on 8 Mar. 2006 and entitled "Fluidic System for a Flow Cytometer" and claims the benefit of U.S. Provisional Application No. 60/792,536, filed 17 Apr. 2006 and entitled "Flow Cytometer System with Unclogging Feature". Both applications are incorporated in their entirety by this reference.

TECHNICAL FIELD

This invention relates generally to the flow cytometer field, and more specifically to an improved fluidic system with an unclogging feature in the flow cytometer field.

BACKGROUND

Typical flow cytometer systems require a very small flow channel, typically less than 0.3 mm in diameter, through which cells or other particles flow in order to be counted. It is not uncommon for the small flow channels to become clogged by debris or clusters of cells. Typically, a clogged flow channel requires the user to halt operation of the flow cytometer system and manually unclog, backflush, clean, and/or replace the flow cell before proceeding. This process can take from minutes to hours and cause significant delay to experiments and inconvenience to the user.

Thus, there is a need for improved flow cytometer systems that minimize or avoid this delay or inconvenience. This invention provides such an improved and useful flow cytometer system.

BRIEF DESCRIPTION OF THE FIGURE

The FIGURE is a schematic representation of the fluidic system with an unclogging feature of the preferred embodiment of the invention.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

As shown in the FIGURE, the fluidic system 10 with an unclogging feature of the preferred embodiment includes a flow channel, a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. At least one of the sheath pump 12 and waste pump 20 and the controller 30 cooperate to propagate a pulsation through the flow channel from the sheath pump 12 and/or waste pump 20 if the flow channel is clogged. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 32, but may alternatively be defined by any suitable system or device. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container.

The flow channel of the preferred embodiment is a very small passageway, typically less than 0.3 mm in diameter, through which cells and sample particles pass during, before, or after interrogation. The term flow channel as is used herein also refers to a flow tip, which is commonly used in the case of sorting flow cytometers. A clog in the flow channel may be the result of anything preventing or altering flow. A full blockage of the flow channel or a partial blockage of the flow channel may both be considered clogs of the flow channel. Examples of material that may clog the flow channel include sample debris, conjugated or clustered cells, or other substances inserted into the flow path of the flow cytometer. The sample may be anything capable of being inserted into the flow path. Samples may include cells, biological materials, or other particles to be assayed, measured, or counted. It should be understood that breaking up a clog in a flow channel includes both the full removal of a blockage from the flow channel as well as the loosening up or partial removal of a blockage from the flow channel, such that—with the addition of a fluid flow—the clog is substantially removed. It should further be understood that cleaning of a flow channel does not preclude the ability of the flow channel to be manually cleaned or manually unclogged.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 34. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 34, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. By varying the flow rates of the sheath pump 12 and the waste pump 20, the controller 30 can induce pulsations within the sheath fluid and the sample fluid. The controller 30 varies the flow rate of the fluids within the system such that each change of the flow rate is accompanied by a commensurate change in the fluid pressure within the system, thereby removing any clogs from the flow channel through these pulsations. Alternatively, the system may include other suitable controllable devices that draw the sample fluid from the sample container into the interrogation zone through the use of a pressure differential.

In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. The preferred controller 30 in this variation is coupled to the variable drive ratio device such that the controller 30 can vary the relative flow rates of the sheath pump 12 and the waste pump 20, wherein varying the pumping rates of the pumps of the system varies the flow rate of the system fluid, and each change of the flow rate of system fluid is accompanied by a commensurate change in the pressure within the system, thereby inducing pulsations in the system fluids at discrete or conditional intervals.

In a second and third variation, the fluidic system 10 of the preferred embodiment may also include a valve 42 located before the interrogation zone 18 and a valve 44 located after the interrogation zone 18. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22 such as by-pass valves, restrictive valves, and/or shutoff valves.

In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. The preferred controller 30 in this variation is coupled to the by-pass valve and adapted to divert a variable amount of fluid through the by-pass valve at discrete or conditional intervals in order to induce pulsations in the system fluids.

In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. The restrictive valve maybe a shutoff valve that alters the fluid flow and, therefore, allows for a variable flow rate of the sheath fluid and/or waste fluid. The preferred controller 30 in this variation is coupled to the restrictive valve and adapted to open/close the shutoff valve at discrete or conditional intervals in order to induce pulsations in the system fluids.

In a fourth variation, the sheath pump 12 and the waste pump 20 are driven by separate motors with separate controls and, therefore, allow for a variable flow rate of the sheath fluid 14 and/or waste fluid 22. The preferred controller 30 in this variation is coupled to one or both of the separate controls of the respective pumps, thereby permitting the controller 30 to induce pulsations in the system fluids at discrete or conditional intervals. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. The controller 30 of the preferred embodiment is connected to the sheath pump 12, the waste pump 20, and/or one or more valves positioned near the respective pumps. The controller 30 is adapted to create pulsations within the fluids through manipulations of the pumping rates of the respective pumps as well as the one or more valves. The controller 30 varies the flow rate of the fluids within the system such that each change of the flow rate is accompanied by a commensurate change in the fluid pressure within the system, thereby removing any clogs from the flow channel through these pulsations. The pressures of the pulsations created are preferably five or six times greater than the baseline pressures maintained in the flow channel, but may alternatively be any suitable pressure to remove any clogs from the flow channel.

Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input.

Control of the flow rate of the fluids within the system can be accomplished through variable pump rates for the respective pumps and/or variable opening or restriction of the one or more valves. Preferably, the controller 30 varies the flow rate at a discrete and repeatable interval, such as between one and ten times per second, creating pulsations with frequencies ranging from 1 Hz to 10 Hz. Alternatively, the controller 30 varies the flow rate at variable intervals, thus creating pulsations with variable frequencies within the system. The controller 30 may alternatively vary the flow rate at any other suitable interval or frequency. The controller 30 is preferably a proportional-integral-derivative (PID) controller, but may alternatively be a proportional-integral (PI) controller, a proportional-derivative (PD) controller, a proportional (P) controller, or any other suitable controller.

The controller 30 may create pulsations at conditional intervals in response to the presence of a clog in the flow channel. The presence of a clog may be detected by a user and signaled through a suitable input device, such as a switch. The presence of a clog may, however, be detected through automated means. Alternatively, rather than in response to the presence of a clog in the flow channel, the controller 30 may create pulsations in anticipation of a clog in the flow channel. Turning on the variable flow rate control in anticipation of a clog may be part of a regular maintenance or cleaning routine that serves to prevent a clog in the flow channel from forming.

The presence of a clog may be automatically detected. In a first variation, the controller 30 may be coupled to a clog detector 46 as shown in the FIGURE. The clog detector 46 functions to detect clogs in the flow channel, in response to which the controller 30 is adapted vary the flow rate of the fluids within the system to remove the clog. The clog detector 46 preferably includes either direct or indirect clog detection devices or methods. The clog detector 46 may alternatively include any suitable device or method.

In a second variation, the fluidic system 10 of the preferred embodiment also includes a pressure sensor 36 that functions to measure a pressure of the sheath fluid 14 as close as possible to the inlet for the sample fluid 26. This measured pressure is an adequate estimate for the pressure of the sample fluid 26. The pressure sensor 36 preferably measures a pressure differential between the top of the drawtube 34 near the flow cell 32 and the bottom of the drawtube 34 near the sample container 28, but may alternatively measure a pressure differential between the drawtube 34 and atmosphere. The controller 30 is preferably connected to the pressure sensor 36 and adjusts the flow rate of the sample fluid 26 based on the measured pressure. The controller 30 may alternatively or additionally be connected to other suitable devices to assist in the control of the flow rate of the sample fluid 26. The pressure sensor 36 functions to detect clogs in the flow channel by detecting a change in pressure, in response to which the controller 30 is adapted vary the flow rate of the fluids within the system to remove the clog. In a third variation, the fluidic system 10 may include a flow meter that functions to measure the flow rate of the sample fluid 26 from the sample container 28 into the interrogation zone 18. The flow meter functions to detect clogs in the flow channel by detecting a change in flow rate, in response to which the controller 30 is adapted vary the flow rate of the fluids within the system to remove the clog.

The pulsations are preferably programmed to turn off when a user-defined or pre-defined parameter has been achieved. Examples of user-defined or pre-defined parameter include time interval, energy output, full or partial return of flow, break up of the clog, or a combination of the above. The process may, however, be fully automated such that the flow cytometer detects a clog, takes appropriate cleaning action, detects a successful unblocking, and then resumes the experiment, with minimal or no user intervention. An example of taking appropriate cleaning action includes suspending the sample flow or a cell count process and turning on the variable flow rate control. An example of resuming the experiment includes turning off the variable flow rate control and resuming sample flow or a cell count process. It is also possible that some clogs in the flow channel will be resistant to being broken up by the variable flow rate control of the preferred embodiment. In these cases, the flow cytometer system preferably signals the user to take appropriate action.

As a person skilled in the art of flow cytometers will recognize from the previous detailed description and from the figures and claims, modifications and changes can be made to the preferred embodiment of the invention without departing from the scope of this invention defined in the following claims.

We claim:
1. A fluidic system for unclogging a flow channel of a flow cytometer including an interrogation zone and a system fluid with a pressure and a flow rate, the fluidic system comprising:
   a sheath pump adapted to pump the system fluid from a sheath container into the interrogation zone;
   a waste pump adapted to pump the system fluid from the interrogation zone into a waste container;
   a motor with motor controls coupled to at least one of the pumps of the fluidic system; and
   a controller connected to the motor and configured to vary the pumping rate of at least one of the pumps of the fluidic system to vary the flow rate of the system fluid and induce a commensurate change in the pressure of the system fluid, to create pulsations within the system fluid that unclog the flow channel of the flow cytometer, wherein the controller is configured to create pulsations that have a pulsation pressure and the pulsation pressure is at least five times greater than the pressure of the system fluid, and wherein the pulsations have a time interval of separation equal to or less than one second.

2. The fluidic system of claim 1 wherein the controller is configured to create the pulsations within the system fluid at a discrete and repeatable interval.

3. The fluidic system of claim 2 wherein the controller is configured to create the pulsations within the system fluid with a frequency ranging from 1 Hz to 10 Hz.

4. The fluidic system of claim 1 wherein the motor includes a variable drive ratio device and the sheath pump and the waste pump are driven by the motor, wherein the sheath pump and the waste pump may be operated at different pump speeds, wherein the controller is connected to the variable drive ratio device such that the controller can vary the pumping rates of the sheath pump and the waste pump.

5. The fluidic system of claim 4 further comprising a by-pass valve located near at least one of the pumps of the system, wherein the controller is operatively connected to the by-pass valve and is configured to divert a variable amount of the system fluid through the by-pass valve.

6. The fluidic system of claim 4 further comprising a restrictive valve located near at least one of the pumps of the system, wherein the controller is operatively connected to the restrictive valve and is adapted configured to open and close the restrictive valve.

7. The fluidic system of claim 1, further including a second motor with second motor controls coupled to at least one of the pumps of the fluidic system.

8. The fluidic system of claim 7, wherein the sheath pump is driven by the first motor and the waste pump is driven by the second motor and wherein the sheath pump and the waste pump may be operated at different pump speeds, wherein the controller is connected to at least one of the first motor controls and second motor controls such that the controller can vary the pumping rates of the sheath pump and the waste pump.

9. The fluidic system of claim 1, wherein the controller is further configured to terminate the creation of pulsations within the system fluid automatically once a pre-defined threshold for a parameter has been reached, wherein the pre-defined parameter is selected from the group consisting of a time interval, an energy output, a full return of flow, a partial return of flow, a break up of the clog, and combinations thereof.

10. The fluidic system of claim 1 wherein the sheath container and the sheath container are vented tanks.

11. The fluidic system of claim 10 wherein the sheath pump and waste pump are positive displacement pumps.

12. The fluidic system of claim 11 wherein the sheath pump and waste pump are peristaltic pumps.

13. A method for unclogging a flow cytometer with an interrogation zone and a fluidic system including a sheath pump, a waste pump, and a system fluid, the method comprising:
controlling the fluidic system including the cooperative steps:
pumping a system fluid from a sheath container into the interrogation zone with the sheath pump,
pumping a system fluid from the interrogation zone into a waste container with the waste pump; and
propagating pulsations through the fluidic system by adjusting the flow rate of the system fluid, the pulsations being separated by a time interval less than one second and having an induced pressure five times greater than a baseline pressure of the fluidic system, wherein adjusting the flow rate of the system fluid includes controlling the pump speed of at least one of the sheath pump and waste pump.

14. The method of claim 13 wherein the step of propogating pulsations includes maintaining a consistent flow rate of at least one of the sheath pump and waste pump.

15. The method of claim 13 including adjusting the flow rate of the sheath pump while maintaining the flow rate of a waste pump in a first situation; and adjusting the flow rate of the sheath pump and adjusting the flow rate of the waste pump in a second situation.

16. The method of claim 13 wherein the step of propagating pulsations includes varying the control of the fluidic system to create discrete and repeatable intervals.

17. The method of claim 16 wherein the repeatable intervals create pulsations with a frequency greater than 1 Hz.

18. The method of claim 17 wherein the sheath pump and waste pump are positive displacement pumps.

19. The method of claim 18 wherein the sheath pump and waste pump are peristaltic pumps.

\* \* \* \* \*